US008105393B2

(12) United States Patent
Suddaby et al.

(10) Patent No.: US 8,105,393 B2
(45) Date of Patent: Jan. 31, 2012

(54) PIGMENT COMPOSITIONS FOR HAIR COLORING

(75) Inventors: Noah A. Suddaby, Westhampton, MA (US); David S. Soane, Chestnut Hill, MA (US); Michael C. Berg, Baltimore, MD (US); Daniel A. Bercovici, Burlington, VT (US)

(73) Assignee: Boston Cosmetics, LLC, Cambridge, MA (US)

( * ) Notice: Subject to any disclaimer, the term of this patent is extended or adjusted under 35 U.S.C. 154(b) by 0 days.

(21) Appl. No.: 12/777,451

(22) Filed: May 11, 2010

(65) Prior Publication Data
US 2011/0083284 A1    Apr. 14, 2011

Related U.S. Application Data

(63) Continuation of application No. PCT/US2008/085470, filed on Dec. 4, 2008.

(60) Provisional application No. 61/005,234, filed on Dec. 4, 2007, provisional application No. 61/051,425, filed on May 8, 2008.

(51) Int. Cl.
*A61Q 5/10* (2006.01)
(52) U.S. Cl. .......... 8/405; 8/435; 8/552; 8/554; 8/637.1; 132/202; 132/208
(58) Field of Classification Search ............... 8/405, 435, 8/552, 554, 637.1; 132/202, 208
See application file for complete search history.

(56) References Cited

U.S. PATENT DOCUMENTS

| | | | |
|---|---|---|---|
| 4,528,283 A | 7/1985 | Lang et al. | |
| 4,559,057 A | 12/1985 | Bogaty et al. | |
| 6,500,446 B1 | 12/2002 | Derrieu et al. | |
| 6,821,509 B2 | 11/2004 | Soane et al. | |
| 7,449,029 B2 | 11/2008 | Nguyen et al. | |
| 2005/0226839 A1 | 10/2005 | Xueying et al. | |
| 2005/0268405 A1 | 12/2005 | Gaelle et al. | |
| 2006/0222609 A1 | 10/2006 | O'Brien et al. | |
| 2007/0065837 A1 | 3/2007 | Meike et al. | |
| 2007/0185281 A1 * | 8/2007 | Song et al. | 525/375 |
| 2007/0269394 A1 | 11/2007 | O'Brien et al. | |

FOREIGN PATENT DOCUMENTS

| | | |
|---|---|---|
| FR | 2773990 A1 | 7/1999 |
| WO | WO 2005025505 A2 | 3/2005 |
| WO | WO 2007078881 A2 | 7/2007 |

OTHER PUBLICATIONS

International Search Report for PCT/US2008/085470 dated Apr. 14, 2009.

* cited by examiner

*Primary Examiner* — Eisa B Elhilo
(74) *Attorney, Agent, or Firm* — Elmore Patent Law Group, P.C.; Mahreen Chaudhry Hoda; Carolyn S. Elmore

(57) ABSTRACT

Compositions and methods relating to the use of pigment compositions are revealed, which can be used to impart color to hair. For instance, treatment formulations that include a pigment-functionalized cationic polymer can be utilized. In some particular instances, a plurality of serially applied treatment formulations is used to improve the characteristics of hair coloring. In addition, other formulations or treatments, such as one or more sealing compositions, or a final coating formulation can also be used to impart other desired characteristics such as treatment durability. Other components of various formulations/compositions are also discussed. Processes for using such compositions/formulations are disclosed. Along with the compositions, kits can be assembled where various compositions/formulations are compartmentalized for storage until the time for application.

36 Claims, No Drawings

PIGMENT COMPOSITIONS FOR HAIR COLORING

CROSS REFERENCE TO RELATED APPLICATIONS

The present application is a continuation of PCT International Application No. PCT/US2008/085470, filed Dec. 4, 2008, entitled "Pigment Compositions for Hair Coloring," which claims the benefit of (i) a U.S. Provisional Patent Application bearing Ser. No. 61/005,234, entitled "Pigment Compositions for Hair Coloring," filed Dec. 4, 2007, and (ii) a U.S. Provisional Patent Application bearing Ser. No. 61/051,425, entitled "Pigment Compositions for Hair Coloring," filed May 8, 2008. The entire contents of all above-listed applications are incorporated herein by reference in their entirety.

FIELD OF THE APPLICATION

This application relates generally to compositions, systems, and methods for applying pigment compositions to hair, which can include applications for hair coloring.

BACKGROUND OF THE APPLICATION

Hair coloring agents presently available fall into one of several basic categories, depending on how they interact with the hair shaft and how long they last. Temporary hair colors coat the surface of the hair shafts and typically wash out within several shampoos. Semipermanent dyes penetrate into the hair shaft, but not as deeply as permanent dyes. While the semipermanent dyes do not rinse off with water, they fade over time and they can be washed out of the hair after about five to ten shampoos. Gradual or progressive dyes (e.g., Grecian Formula 16), usually marketed to men, contain lead acetate [$Pb(CH_3COO)_2$], which penetrates the hair cuticle. The $Pb^{2+}$ ions react with sulfur atoms in the hair shaft proteins to form lead sulfide (PbS), which is a dark color. More frequent use leads to an increased darkening of the hair. Finally, permanent hair dyes are available for long-lasting color change. These formulations penetrate the hair shaft to deposit pigments therein, so they cannot be washed out. Before the coloring agents of a permanent hair dye can penetrate the hair shaft, the cuticle of the hair shaft must be opened so that the pigments can gain access to the interior.

For example, a permanent hair-color product may consist of two chemical components that are packaged separately and mixed together immediately before being applied to the hair. One component can be a solution of hydrogen peroxide in a water or emollient base. The second component can be an ammonia-based solution of dye intermediates and/or preformed dyes or couplers. Formulations for permanent dyes generally include oxidative hair dye precursors that diffuse through the cuticle of the hair and into the cortex, where they can react with each other in the presence of oxidizing agents, thereby forming larger dye molecules. The large size of the dye molecules prevents them from diffusing out of the cortex, so that the hair color change is permanent. These reactions typically require a pH of approximately 10 in the presence of an oxidizing agent.

Exemplary dye intermediates include small molecules such as ortho- or para-diaminobenzenes, aminohydroxybenzenes, and to a lesser extent dihydroxybenzenes that develop color on oxidation. The color couplers include small molecules such as various phenols, meta di-substituted phenylenediamines and phenyleneaminophenols, and certain various resorcinol (1,3-dihydroxybenzene) derivatives. The couplers do not oxidize readily, but they react with the oxidized primary intermediates to yield a greater range of colors.

Under typical circumstances, the hydrogen peroxide solution and the ammonia-dye solution are mixed together and promptly applied to the hair. The ammonia in the mixture causes the hair shaft to swell, thereby separating the scales of the hair cuticle. When this happens, the dye precursors can penetrate the cuticle. The dye precursors complete their chemical reactions once they have gained access to the interior of the hair shaft. Dyes bind covalently to proteins within the hair shaft.

Variations in hair color may be obtained by varying the dye intermediates. For instance, higher concentrations of certain intermediates may yield darker hair colors. Adding resorcinol as an intermediate may make a color more yellow, while adding 4-amino-2-hydroxytoluene will make the color redder. Dyes added along with the oxidation dye intermediates may make a tone brighter or more intense. For example, using a dye like 2-nitro-p-phenylenediamine may yield a bright orange color.

Many of the chemicals used in permanent dye systems have potential toxicities. As an example, the primary amine used in oxidative dye systems is generally paraphenilenediamine (PPD). There are concerns that PPD may be implicated in carcinogenesis and mutagenesis. As another example, there is evidence of toxicity from dye system precursors such as the coupler resorcinol. Furthermore, the high pH and the use of hydrogen peroxide lead to conditions that damage the hair shaft and irritate the scalp and skin.

Certain chemicals used in semi-permanent hair color systems have potential toxicities as well. As an example, coal tar dyes are used for semi-permanent hair coloring. Many coal tar dyes and mono-azo/di-azo dyes that yield red and red-orange shades are suspected of carcinogenesis, teratogenesis and/or mutagenesis. Dyes used in semi-permanent preparations may also stain scalp and skin.

Natural dyes have disadvantages for hair coloring when compared to the synthetic preparations described above. A major disadvantage of natural dyes is their tendency to produce dull color shades. In addition, natural dyes are shampoo-resistant than synthetic preparations. Plants provide natural sources for dyes, but contain low concentrations of appropriate colorants. Moreover, dyes that are retrieved from plants may be impure and/or may have poor solubility. As a result, natural dyes may require prolonged application times to yield desirable, natural-looking hair color. In addition, most natural hair dyes are provided as powders, which are inconvenient for consumers or hairdressers to apply.

There remains a need in the art, therefore, for safe and effective hair coloring products and processes. There remains a further need in the art for hair color formulations that use safe, non-toxic and environmentally benign materials.

SUMMARY

Embodiments of the invention are drawn to compositions and methods for modifying hair (e.g., coloring hair) using pigments. Such pigments can be disposed in various forms, such as a pigment-functionalized cationic polymer. These pigments can be applied to hair in a manner that can potentially mitigate or eliminate various disadvantages associated with coloring dyes. Other compositions are also provided that help enhance the use of such pigment compositions. Kits and methods for utilizing such compositions are also within the scope of the present invention.

Some embodiments are drawn to methods for coupling hair with pigment. Hair can be treated once, or serially, with one or more treatment formulations. When hair is treated more than once, the treatment formulations can be of the same type or differing types. In some instances, hair can be rinsed, dried, or otherwise washed with water or a typical shampoo after the hair is treated with a treatment formulation, which can help remove excess treatment formulation. The treatment formulation(s) can be coupled to the hair.

A treatment formulation can include a pigment-functionalized cationic polymer. Cationic polymers can include amine-containing polymers. Specific examples of cationic polymers that can be included are any one or more of chitosan, polyalkyleneimene, poly(vinyl amine), poly(allyl amine), poly(lysine), cationic cellulose derivatives, and cationic starch derivatives. In some instance, the cationic polymer can be crosslinked, e.g., through the use of crosslinkers that can be included with the treatment formulation or added subsequently. Treatment formulation(s) can also utilize solvents such as an aqueous solvent, an alcoholic solvent, and/or a silicone-containing solvent. Treatment formulations can also include one or more of a surfactant, a foam, a UV blocker, a fragrance, and a viscosity modifier.

In some embodiments, one or more sealing compositions can be applied to the hair after at least one of the treatment formulations treats the hair; this can potentially enhance coupling of the treatment formulation(s) to the hair. Sealing composition(s) can act to increase the abrasion resistance of one or more of the treatment formulations when applied to hair, and/or increase the hydrophobicity of the hair. The sealing composition(s) can include an anionic component such as a polyanion. Polyanions can include a maleic anhydride group and/or carboxylic acid group. Example of polyanions include poly(isobutylene-alt-maleic acid), poly(isobutylene-alt-maleic anhydride), pectin, xanthan gum, carboxy methyl cellulose, polyacrylic acid, and styrene maleic anhydride.

In some embodiments, a final coating formulation can be applied to hair after treating hair with one or more treatment formulations. Final coating formulations can include any one or more of an emulsified hydrophobic component, a crosslinker, a silicone-containing component, a hydrophobic macromer, a polycation, a plasticizer, and a combination of an amine group and a silicone group.

In some embodiments, hair can be pretreated with an acid composition and/or a basic composition before the hair is treated with one or more treatment formulations. Acidic compositions can exhibit a pH below about 5.5 (e.g., between about 2 and about 5.5), while basic compositions can exhibit a pH above about 7.5 (e.g., between about 7.5 and about 10).

Other embodiments are drawn to kits for coupling pigment to hair, which can include pigments used for hair coloring. A kit can include one or more treatment formulations, and one or more sealing compositions. Optionally, kits can include a final coating composition and/or a pretreatment composition that can be an acidic or basic composition. The formulations and compositions can be separately packaged, which can isolate the materials from one another until they are applied to hair. The formulations' and compositions' characteristics can include any of the components and functions described herein.

DETAILED DESCRIPTION

Disclosed herein are compositions, systems and methods for coloring hair by using pigments instead of dyes. Pigments can be more inert than dyes, resulting in a formulation that is more consumer and environmentally friendly. Pigments can, in some instances, hold their color for a longer period of time relative to dyes, resulting in a more lasting coloring. Pigments' use as a hair coloring treatment can be complicated by their insoluble nature in water. Accordingly, some embodiments are directed to treatment formulations that allow the pigments to be delivered in an aqueous solvent to hair (e.g., by delivering the pigments as a pigment-functionalized cationic polymer that can be dispersed in an aqueous solvent).

In embodiments, hair may be colored by applying a treatment formulation to the hair, where the treatment formulation comprises a pigment composition. The pigment composition can include pigment particles, a polycation, and a solvent (e.g., water). The pigment composition can include one or more pigments. As used herein, the term "pigment" can refer to any type particle colorant (any color including white or black) that is insoluble in water. Pigments can be organic, inorganic, or a combination of both in nature. A mixture of pigments in the pigment composition can produce various shades of color. In embodiments, the primary particle size for a pigment can be less than one micron, though other particle sizes can also be utilized in some embodiments.

As used herein, the term "polycation" refers to an entity with a net positive charge containing repeat units. In a treatment formulation, a polycation can be coupled to, or otherwise attached to, a pigment as a pigment-functionalized cationic polymer. As used in the present application and unless otherwise specifically delineated otherwise, the terms "couple" and "attach," are synonymous and refer to an attractive association keeping two or more entities together. The attractive association can be due to any number of attractive forces including, but not limited to, covalent bonding, ionic and/or electrostatic forces, Van der Waals attraction, other intermolecular forces, and steric considerations (e.g., polymers entangling and/or surrounding other entities).

The term "polymer" refers to a molecule comprising a plurality of repeat units or monomers. In some instances, the polymer can have a minimum plural number of repeat units, such as greater than about 10, 15, 20, 25, 30, 40, or 50 repeat units. A polymer can comprise one or more distinct repeat units. For example, a "copolymer" refers to a polymer having two or more distinct repeat units. Repeat units can be arranged in a variety of manners. For example, a homopolymer refers to a polymer with one type of repeat unit where the repeat units are adjacently connected. In another example, a plurality of different repeat units can be assembled as a copolymer. If A represents one repeat unit and B represents another repeat unit, copolymers can be represented as blocks of joined units (e.g., A-A-A-A-A-A . . . B-B-B-B-B-B . . . ) or interstitially spaced units (e.g., A-B-A-B-A-B . . . or A-A-B-A-A-B-A-A-B . . . ), or randomly arranged units. Of course, these representations can be made with 3 or more types of repeat units as well. In general, polymers (e.g., homopolymers or copolymers) include macromolecules in a broad range of configurations (e.g., cross-linked, linear, and/or branched).

As an example, a polycation may be an amine containing polymer having primary, secondary, tertiary, and/or quaternary amines. Other examples of polycations can include polymers having polycationic segments as described in an International Patent Application entitled "Compositions and Methods for Treating Hair," filed Nov. 28, 2007, bearing International Application Number PCT/US2007/24511, and having inventors David S. Soane, Michael C. Berg, and William A. Mowers, which is hereby incorporated herein by reference in its entirety. Non-limiting examples of polycations include chitosan, polyalkyleneimene, poly(vinyl amine), poly(allyl amine), poly(diallydimethylammonium chloride), poly(lysine), cationic cellulose derivatives, cationic starch derivatives, and polymers of arginine. In a particular example, polyethyleneimine segments can comprise at least a portion of a polycation. Polymers can also include linear polymers (e.g., linear polyethyleneimine, branched polymers, and mixtures of linear and branched polymers in various embodiments.

In some embodiments, the molecular weight of a polycation can range from about 1,000 to 10,000,000 daltons. In embodiments, the molecular weight of the polycation is between about 10,000 and 500,000 daltons. Certain polyamines like chitosan are not characterized by molecular weight, but by viscosity. For chitosan, as an example, a viscosity between 10 cp (2% in acetic acid solution) and 1600 cp (1% in acetic acid solution) is desirable when it is used as a polycation for these systems and methods.

One or more other components can also be added to a treatment formulation to provide one or more additional properties. In embodiments, additional solvents such as alcohol may be added to the treatment formulation to aid drying if desired. In some embodiments, surfactants can be added to a treatment formulation to form an emulsion. This can be beneficial when the formulation is delivered as a foam. Surfactants can be any compatible type, such as a nonionic surfactant or a cationic surfactant. Other potential components can include any one or more of UV blockers, fragrances, viscosity modifiers, and other materials that are can be utilized in a hair treatment formulation, including those known to one skilled in the art. While embodiments disclosed herein may discuss these various components with respect to their presence in one or more treatment formulations, it is understood that these components can also be included in other formulations/compositions, to form other embodiments, as described herein.

Viscosity modifiers can be used in some embodiments to substantially enhance the ability of a treatment formulation to be worked into hair, resulting in substantially easier hair treatment and/or improved adhesion to hair. Thickening agents such as glycerin, polyethylene glycol, polypropylene glycol, nonionic polymers, or silica-based materials (e.g., fumed silica) may be added to increase the viscosity of the composition; two or more such agents can be utilized in combination to form a thickening agent.

The polycation in a formulation may be crosslinked after application to the hair. Without being bound to any particular theory, crosslinking of a polymer in a formulation/composition can potentially enhance the functionality of a hair coloring technique. Crosslinking can potentially tighten a polymer network, which can enhance attachment of pigment and polymer and/or enhance attachment between the polymer and some other component (e.g., sealing composition, final coating formulation, or other treatment formulation). Such crosslinking can be achieved using one or more crosslinkers, e.g., any compound with more than one functional group that can react with groups on the polycation. For instance, the crosslinker can include one or more groups that can react with an amine of a polyamine to induce crosslinking of chains. As non-limiting examples, the functional group can be an epoxy, anhydride, acid chloride, ethyleneimino, aldehyde, (hemi) acetal, (hemi)aminal, ketone, alpha-halo ketone, alpha-hydroxy ketone, lactone, thio lactone, isocyanate, thiocyanate, N-hydroxy succinimide ester, imide, imine, imidate, oxazoline, oxazolinium, oxazine, oxazinium, pyridyl thio, and thiosulfate. Diepoxides such as 1,4 butanediol diglycidyl ether and hydroxyalkylureas such as dimethyloldihydroxy -ethyleneurea can be especially advantageous.

While crosslinkers can often be utilized in a treatment formulation, in some embodiments the crosslinkers can also be included in any other formulation or composition, e.g., in a final coating formulation or a sealing composition directly after a treatment formulation is applied. In some embodiments, the crosslinker can be applied as a separate step (e.g., independent of the formulations/compositions described herein) after one or more treatment formulations are used to treat hair. As well, crosslinkers can be used to crosslink other polymers in various compositions/formulations disclosed herein.

In accordance with the systems and methods described herein, the treatment formulation may be used to treat the hair using any method that brings allows it to be delivered to the hair. Such methods include brushing it into the hair, dipping the hair into the formulation, spraying the formulation onto the hair, or applying the formulation as a foam or gel and/or emulsion. In some embodiments, a treatment formulation can be applied to hair as multiple formulations (e.g., applying one formulation having the cationic polymer and another formulation having pigment), though oftentimes it is applied as a single formulation. In some embodiments, after the treatment formulation has been applied to the hair, the hair can be rinsed with water to remove excess colorant/pigment composition. Excess colorant/pigment composition can also be removed by blot drying or airdrying followed by a brush out with a hair brush. A treatment formulation including a pigment composition can then be coupled to the hair, techniques such as those described herein.

In several embodiments, hair can be serially treated with multiple treatment formulations. The multiple treatment formulations, which can be of the same type or different, can be especially advantageous in helping improve the coloring of hair vis-à-vis using only one treatment formulation. Applicants have discovered that the serial application of multiple treatment formulations can result in a greater variety of colorings and/or improve the durability of such coloring and/or impart other characteristics such as hydrophobicity, which were not realizable with single treatment formulations.

Hair treated with a treatment formulation can be exposed to a sealing composition for enhancing attachment of pigment to the hair. This sealing composition can be applied after removal of excess colorant, in some embodiments. In some instances, the sealing composition can coat the hair shaft that is treated with the treatment formulation, rendering the treated hair more resistant to abrasion (e.g., color removal by friction) and/or increasing the durability of the treatment formulation (e.g., more resistant to water or other solvents that can cause removal of color from hair). For instance, the sealing composition can help decrease friction imparted to the treated hair to help increase color durability. The treatment with the sealing composition can also potentially remove unattached pigment. When multiple treatment formulations are applied to the hair, one or more types of sealing compositions can be applied after any number of the treatment formulations in any appropriate order.

In some embodiments, the sealing composition can include an anionic component. Examples of anionic components include entities having one or more carboxy, sulfate, sulfonate, phosphate or phosphonate moieties. Examples of such polymers include DNA, poly(acrylic acid), poly(itaconic acid), poly(maleic anhydride), copolymers containing maleic anhydride units, a polymer with —$C_6H_5COOH$ groups, poly (methacrylic acid), or poly(styrene sulfonate, sodium salt). In particular embodiments, a sealing composition includes a polyanion (i.e., a polymer with a net negative charge). In some instances, such an anionic component can bind with a polycation, for example, simply through electrostatic interactions. The sealing composition can also, or alternatively, include other components bindable to one or more components of the treatment formulation such as polymers having moieties capable of interacting with a polycation and/or the pigment. Such binding can be through electrostatic interactions, Van der Waals forces, covalent bonding, other intermolecular forces, and combinations of any such binding mechanisms. In certain instances, the sealing composition reacts with the polycation to bind and coat the pigment to the hair shaft.

In embodiments, the sealing composition can include components that impart hydrophobicity. In certain instances, a sealing composition may not be completely water-insoluble, but a hydrophobic character remains. In such instances, for example when the sealing composition comprises an appropriate polymer, it is desirable that the polymer not dissolve readily in water. As examples, polymers in a sealing composition can include maleic anhydride groups and/or carboxylic acid groups. Specific examples include styrene maleic anhydride polymers, poly[(isobutylene-alt-maleic acid), ammonium salt)-co-(isobutylene-alt-maleic anhydride)], and cellulosics containing carboxylic acid groups such as pectin, xanthan gum, or carboxy methyl cellulose. The polymer's molecular weight can range from about 1,000 to 10,000,000 daltons. In embodiments, the second polymer's molecular weight is between about 10,000 and 500,000. In embodiments, the second polymer can be applied in an aqueous or alcohol solvent. The polymer can be applied to the hair using any method that brings it into direct contact with the hair. For example, the polymer may be brushed into the hair, sprayed onto the hair, applied as a solution, a gel or a foam, or other disposition.

In an alternate embodiment, the treated hair may be exposed to a sealing composition including a second polymer following the application of the treatment formulation and the removal of excess pigment. According to this embodiment, the cationically-charged pigment-bearing hair may be coated with a polyanion that reverses this charge. Following application of the treatment formulation, the hair may be rinsed and dried before applying the second polymer or rinsed only.

As used herein, the term "polyanion" includes any polyanion or copolymer that is anionic so that this second polymer treatment reverses the charge of the treated hair shaft. As examples, second polymers may include carboxylic acid groups, sulfuric acid groups, and/or phosphoric acid groups in its repeat units. Specific examples include polyacrylic acid, polymethacrylic acid, sulfonated polystyrene, pectin, carboxy methyl cellulose, xanthan gum, and polyacrylic acid—polyacrylamide copolymers. The second polymer's molecular weight can range from about 1,000 to 10,000,000 daltons. In embodiments, the second polymer's molecular weight is between about 10,000 and 500,000.

In some particular embodiments, there may be a first coloring step and a second coating step, with the two steps providing sufficient intensity and durability of the color. In other embodiments, the coloring step and the polyanion coating step may be repeated to obtain a deeper or more durable color, e.g., using two treatment formulations where each treatment formulation employs a different color pigment particle to give a particular coloring effect. Applicants have found that multiple applications of treatment formulation and sealing composition together can be substantially better than use of a single ensemble of treatment formulation and sealing composition. For instance, one sealing composition can act to help binding of hair while another sealing composition can impart other properties such as hydrophobicity. Thus, according to this practice of the method, there can be a first coloring step, a second step of polyanion coating, a third step of coloring, and a fourth step of polyanion coating. The combination of application steps may be repeated an appropriate number of times to achieve enhanced color and/or texture and/or other properties.

In embodiments, the second polymer can be applied in an aqueous or alcohol solvent. The second polymer can be applied to the hair using any method that brings it to treat the hair. For example, the second polymer may be brushed into the hair, sprayed onto the hair, applied as a mixture, a gel or a foam, or the like. As well, a sealing composition can be applied as multiple compositions or a single composition.

For any of the coloring treatments described herein (e.g., a single step treatment, the two-step process, or the four-step process), a final coating formulation may be applied (e.g., following application of the polyanion coating or even just after the coloring formulation without an anionic treatment). In some embodiments, the final coating formulation comprises a polycation. Optionally, the final coating formulation may further comprise an emulsified hydrophobic component. In embodiments, the hydrophobic component may be a silicone components—such as a silicone containing polymer. In other embodiments, the final coating formulation comprises a plasticizer that is compatible with the polycation to soften the resulting polycation film. Examples of such materials include small molecule plasticizers such as triacetin along with polymers such as but not limited to polypropylene glycol, polyvinyl alcohol, partially hydrolyzed polyvinyl acetate, and polyethylene glycol.

Advantageously, a polycation such as an amine-containing polymer (e.g., chitosan and/or polyethyleneimine and/or any of the amine-containing polymers discussed with respect to the treatment formulations) may be used for the polycation coating stage. In some instances, the polycation formulation includes an emulsified nonreactive silicone. Silicone added to the coating can improve performance of the overall formulation by acting as a lubricant to prevent clumping of the processed hairs and to facilitate their being combed out without tangling (e.g., washability of the hair). Without being bound by theory, it is understood that the pigments, coating compositions and other materials are all bound together electrostatically, thereby minimizing or avoiding destructive interaction with the hair shaft.

In some embodiments, as a final coating step, an aqueous mixture comprising polycations or polycations surrounding and stabilizing a core composed of a hydrophobic macromer is applied to the previously treated hair. This final step can act to further seal in the pigment and reduce rub-off and/or increase resistance to rub-off during shampoo washes. The polycation can either be a homopolymer or copolymer that has monomers that contain either primary, secondary, tertiary, or quaternary amines. Examples of such cationic polymers include polyethyleneimine (either linear or branched), poly(vinyl amine), poly(allyl amine), chitosan, cationic cellulose derivatives, and cationic starch derivatives. The molecular weight of a polycation can range from about 1,000 to 10,000,000 daltons. In embodiments, the molecular weight of the polycation is between about 10,000 and 500,000 daltons. Certain polyamines like chitosan are not characterized by molecular weight, but by viscosity. For chitosan, as an example, a viscosity between 10 cp (2% in acetic acid solution) and 1600 cp (1% in acetic acid solution) is desirable when it is used as a polycation for these systems and methods.

In embodiments, the hydrophobic macromer contains a functional group that reacts with the amine once the composition is dried and/or heated. As examples, the functional group can be an epoxy, anhydride, acid chloride, ethyleneimino, aldehyde, (hemi)acetal, (hemi)aminal, ketone, alpha-halo ketone, alpha-hydroxy ketone, lactone, thio lactone, isocyanate, thiocyanate, N-hydroxy succinimide ester, imide, imine, imidate, oxazoline, oxazolinium, oxazine, oxazinium, pyridyl thio, and thiosulfate. In other embodiments, the hydrophobic macromer can interact with the polycation electrostatically. For instance, the hydrophobic macromer can contain monomeric groups such as sulfuric acid, phosphoric acid, or carboxylic acid. Desirably, the hydrophobic macromer core is not miscible with water or has limited miscibility. In embodiments, the hydrophobic macromer can have a $T_G$ below room temperature. In embodiments, the hydrophobic macromer can have a small enough molecular weight that it can be easily emulsified, so that it can provide a soft feel to the hair. Examples of suitable polymers include reactive silicones and elastomeric polymers such as copolymers containing polyisoprene. Desirably, the concentration of the hydrophobic component is low enough that it does not make a continuous phase in the polycation mixture. The ratio of hydrophobic macromer to polycation can vary depending on the application method.

The overall concentrations of polymers in each formulation/composition applied according to these systems and methods may vary from 0.1% up to 50% depending on the specific polymers being used and the desired viscosity for application. After application, the hair is dried using any technique such as air-drying or blow drying. A gentle rinse can be performed after the final step, but it is not necessary As part of the coloring process, or following the process, the hair may be shampooed and/or conditioned using materials familiar to those of ordinary skill in the art, for example to improve the look and feel of the hair.

With regard to the various formulations and composition described herein, solvents which can be aqueous or alcoholic in nature can be utilized, as previously alluded to. In some embodiments, such formulations/composition (e.g., a treatment formulation) can include the use of a siloxane-containing small molecule solvent such as a cyclosiloxane. Without being bound by any particular theory, a siloxane-containing solvent can be advantageous in some circumstances by spacing apart the polycations of a treatment formulation, resulting in more even treatment formulation distribution. The siloxane can also improve the "touch" of the hair, while excess can evaporate. The use of siloxane-containing solvents such as a cyclosiloxane can also be beneficial when forming a composition/formulation in the disposition of a foam or other emulsion.

In embodiments, pretreating the hair can also improve the interaction of the treatment formulations disclosed herein with the hair. For example, a pretreatment with an acidic or basic composition can be advantageous in coupling the treatment formulation to the hair. Without being bound by any particular theory, a pretreatment can cause a hair shaft to swell, which can aid in the coupling between the hair and a formulation/composition. The acid or base composition can be any that is compatible with hair. An example of an acidic composition is one that comprises citric acid. An example of a basic composition is one comprising ammonium. In some embodiments, an acidic pretreatment composition can exhibit a pH below about 5.5 while not being so low as to damage hair (e.g., a pH in a range between about 2 and about 5.5). In other embodiments, a basic pretreatment composition can have a pH above about 7.5 but not so high as to damage the hair (e.g., a pH in a range between about 7.5 and about 10).

It is understood that various embodiments can utilize any number of the treatment formulations, sealing compositions, final coating composition, pretreatment steps etc. in any consistent combination. For instance, in a first example, a method can include utilizing three series of treatments with a treatment formulation followed by a sealing composition using polyacrylic acid with varying pHs for each composition. In another example, the first example is modified by a final coating composition using an amine-containing polymer. In yet another example, a pretreatment with an acid or base composition can be followed by a treatment formulation and a final coating composition using a polycation such as chitosan. As well, these examples can be utilized with or without crosslinkers in any of the compositions/formulations. Accordingly, the invention is not to be limited to the explicitly enunciated embodiments in the present application.

While many embodiments discussed herein refer to processes for using the various formulations and compositions discussed herein, it is understood that embodiments of the invention also extend to the particular formulations and compositions disclosed herein. Accordingly, some embodiments are directed to any of the treatment formulations, sealing compositions, and final coating formulations described herein, which can include any compatible variation and multiplicity of the components described herein.

In some particular embodiments, kits that include any combination of the treatment formulations, sealing compositions, and final coating formulations can be formed. Such kits can be especially useful in separating various formulations/compositions until they are ready for use as some combinations may react and/or interact with one another. Accordingly, formulations/compositions in a kit can be separately packaged from one another, i.e., isolated from each other in any manner including using techniques known to those skilled in the art. Such isolation can also be important in making a kit for use of a consumer. Separation of the various compositions/formulations can aid prevention of consumer confusion regarding the order in which compositions/formulations are to be applied, along with helping direct a consumer regarding the handling of particular compositions/formulations.

For instance, a kit can include one or more treatment formulations that can each separately packaged. When one or more sealing compositions and/or final coating formulations are included, these can also be each separately packaged. Separate packaging can include discrete containers for each formulation/composition, container(s) having isolated compartments for separating compositions/formulations, or a combination of these techniques. Other techniques, including those known to one skilled in the art, can also be employed.

EXAMPLES

Materials
BPEI: Poly(ethyleneimine) solution 50% (w/v) in water
   Sigma Aldrich P3143-500ML
   St. Louis, Mo.
Carbon Black: Unipure carbon black, 99% pure dye
Red Iron Oxide:
Brown Iron Oxide:
MA165K: Poly[(isobultylene-alt-maleic acid), ammonium salt)-o-(isobutylene-alt-maleic anhydride)]
   Aldrich 531367-250G
   St. Louis, Mo.
SMA3000H: Styrene maleic anhydride resin, cumene end capped, ammonium salt (52720-34-0)
   Sartomer SMA 3000H
   Warrington, Pa.

SF8411: Dow Corning silicone (Multiepoxide functional siloxane)
Chitosan: Primex—cg110 and cg800
PEG-DGE (Polyethylene Glycol-Diglycidyl ether)
  Sigma Aldrich 475696-100ML
  St. Louis, Mo.
Citric acid 0.1M
  Sigma Aldrich 251275-500G
  St. Louis, Mo.
Epoxy Modified Polydimethylsiloxane (PDMS-epoxy)
  GE Coatosil 2810 material: 72507
  Friendly, W.V.
Decamethylcyclopentasiloxane (DMCPS)
  Dow Corning 245 FLUID
  Midland, Mich.

Example 1

Carbon Black Slurry 3.75 gm of carbon black and 250 mg of BPEI were added to 67.5 mL of water. To this slurry, 30 g of ceramic mixing beads were added. The slurry was then bead-milled for 5 minutes on a FlakTek Model DAC 150 FVZ-K. A dispersion of carbon black was obtained.

Example 2

Blonde Hair Colored Black

The carbon black slurry from Example 1 was combed into a swatch of blonde hair until the individual hairs were coated with the black slurry. The swatch was then rinsed in water and dried with a hair dryer. The hair was dyed a black color that did not come off with water washing.

Example 3

Blonde Hair Colored Black With 50% Diluted Slurry 15 gms of the carbon black slurry from Example 1 was added to 15 mL of deionized water and then stirred for 2 minutes on a FlakTek Model DAC 150 FVZ-K. The resulting diluted slurry was then combed into 3 swatches of blonde hair until the individual hairs were coated with the black slurry. The swatch was then rinsed in water and dried with a hair dryer. The hair was dyed a black color that did not come off with water washing.

Example 4

Blonde Hair Colored Black With 33% Diluted Slurry

The carbon black slurry from Example 3 was added to 15 mL of deionized water and then stirred for 2 minutes on a FlakTek Model DAC 150 FVZ-K. The resulting diluted slurry was then combed into 3 swatches of blonde hair until the individual hairs were coated with the black slurry. The swatch was then rinsed in water and dried with a hair dryer. The hair was dyed a black color that did not come off with water washing.

Example 5

Maleic Anhydride Polymer Coating on Colored Hair

A swatch of blonde hair colored black in the manner of Example 2 was then given a polymer coating by dripping 2mL of a 1% aqueous solution of maleic anhydride polymer (MA165K) over the swatch with a pipette. Excess polymer solution was gently squeezed out and the swatch was dried with a blow dryer. The hair was colored a black color that did not come off with water washing and was resistant to being rubbed off with mild abrasion.

Example 6

Styrene Maleic Anhydride Polymer Coating on Colored Hair

A swatch of blonde hair colored black in the manner of Example 2 was then given a polymer coating by dripping 2 mL of a 1% aqueous solution of styrene maleic anhydride polymer (SMA300H) over the swatch with a pipette. Excess polymer solution was gently squeezed out and the swatch was dried with a blow dryer. The hair was colored a black color that did not come off with water washing and was resistant to being rubbed off with mild abrasion.

Example 7

Iron Oxide Slurry 3 gm of red iron oxide, 0.75 g brown iron oxide, and 250 mg BPEI were added to 67.5 mL of water. To this slurry, 30 g of ceramic mixing beads were added. The slurry was then bead-milled for 5 minutes on a FlakTek Model DAC 150 FVZ-K. A dispersion of iron oxide was obtained.

Example 8

Blonde Hair Colored Red

The iron oxide slurry from Example 7 was combed into a swatch of blonde hair until the individual hairs were coated with the red slurry. The swatch was then rinsed in water and dried with a hair dryer. The hair was dyed a red color that did not come off with water washing.

Example 9

Polyacrylic Acid Anionic Sealant

The carbon black slurry from Example 1 was combed into a swatch of blonde hair until the individual hairs were coated with the black slurry. The swatch was then rinsed in water. Then approximately 1 mL of a 1% solution of polyacrylic acid (PAA) was dripped onto the hair and worked in with fingers. This was then rinsed out, and the hair was dried with a hair dryer. The hair was colored a black color that did not come off with water washing and was resistant to being rubbed off.

Example 10

Chitosan Cationic Sealant

A 2% solution of chitosan (cg110) that had been solvated with benzoic acid was added to SF8411 silicone and deionized water and then homogenized to make an emulsion containing 0.5% chitosan and 0.5% silicone.

Example 11

Three Step Color and Sealing

A swatch of blonde hair was treated with the carbon black slurry from Example 1 and the PAA solution from Example 9 according to the procedure set forth in Example 9. Then approximately 1 mL of the chitosan/silicone emulsion from Example 10 was added to the hair using a pipette, and then it was dried using a hair drier. The hair was colored black and the color was resistant to being removed by washing with shampoo and was resistant to being rubbed off with mild abrasion.

Example 12

Five Step Color and Sealing Applied to Blonde Hair

The carbon black color solution from Example 1 was brushed onto a swatch of blonde hair until all the individual hairs appeared black. Then the hair was thoroughly rinsed with water. Then approximately 1 mL of the 1% PAA solution from Example 9 was added to the hair using a pipette. The hair was then dried with a blow dryer. Then the coloring step and the PAA sealing step were each repeated once again with a water rinse in between the two.

The hair was dried again with a blow dryer. Then approximately 1 mL of the chitosan/silicone emulsion from Example 10 was added to the hair using a pipette, and then it was dried using a hair drier. The hair was colored black and the color was resistant to being removed by washing with shampoo and was resistant to being rubbed off with mild abrasion.

Example 13

Five Step Color and Sealing Applied to Grey Hair

The procedure in Example 12 was repeated using a hair swatch that was a blend of 50% dark hairs and 50% grey hairs. This resulted in hair that was colored black and was resistant to washing and being rubbed off with abrasion.

Example 14

Five Step Color and Sealing Applied to Grey Hair (Streamlined)

The carbon black color solution from Example 1 was brushed onto a hair swatch of 50% grey hair and 50% black hair until all the individual hairs appeared black. Then the hair was thoroughly rinsed with water. Then approximately 1 mL of the 1% PAA solution from Example 9 was added to the hair using a pipette. This was worked in using fingers, and then it was rinsed out. Then the coloring step and the PAA sealing step were each repeated once again with a water rinse in between the two. Then approximately 1 mL of the chitosan/silicone emulsion from Example 10 was added to the hair using a pipette, and then it was dried using a hair drier. The hair was colored black and the color was resistant to being removed by washing with shampoo and was resistant to being rubbed off with mild abrasion.

Example 15

Chitosan/Silicone Emulsion Ratio

A 2% solution of chitosan (cg110) that had been solvated with benzoic acid was added to SF8411 silicone and deionized water and then homogenized to make an emulsion containing 0.5% chitosan and 2% silicone.

Example 16

Five Step Color and Sealing Applied to Grey Hair (Streamlined)

The procedure set forth in Example 14 was performed using the chitosan/silicone emulsion prepared as described in Example 15. This resulted in hair that was colored black and was resistant to washing with shampoo and being rubbed off with mild abrasion.

Example 17

Carbon Black Slurry With Glycerin 3.75 gm of carbon black were added to 75 g of glycerin. 7 mL deionized water were added to 250 mg of BPEI, and this solution was then added to the carbon black and glycerin. To this slurry, 30 g of ceramic mixing beads were added. The slurry was then bead-milled for 5 minutes on a FlakTek Model DAC 150 FVZ-K. A viscous dispersion of carbon black was obtained.

Example 18

Viscous Carbon Black on Grey Hair

The procedure set forth in Example 14 was performed using the carbon black slurry prepared as described in Example 17. The hair was colored black and was resistant to washing with shampoo and being rubbed off with mild abrasion.

Example 19

Carbon Black Slurry With Glycerin (Half-Strength Carbon Black)

1.87 gm of carbon black were added to 83 g of glycerin. 7 mL deionized water were added to 250 mg of BPEI, and this solution was then added to the carbon black and glycerin. To this slurry, 30 g of ceramic mixing beads were added. The slurry was then bead-milled for 5 minutes on a FlakTek Model DAC 150 FVZ-K. A viscous dispersion of carbon black was obtained.

Example 20

Viscous Carbon Black on Grey Hair (Half-Strength Carbon Black)

The procedure set forth in Example 14 was performed using the carbon black slurry prepared as described in Example 19. The hair was colored black and was resistant to washing with shampoo and being rubbed off with mild abrasion.

Example 21

Carbon Black Slurry With Glycerin (Two-Thirds Strength Carbon Black)

2.75 gm of carbon black were added to 75 g of glycerin. 7 mL deionized water were added to 250 mg of BPEI, and this solution was then added to the carbon black and glycerin. To this slurry, 30 g of ceramic mixing beads were added. The slurry was then bead-milled for 5 minutes on a FlakTek Model DAC 150 FVZ-K. A viscous dispersion of carbon black was obtained.

Example 22

Viscous Carbon Black on Grey Hair

The procedure set forth in Example 14 was performed using the carbon black slurry prepared as described in Example 21. The hair was colored black and was resistant to washing with shampoo and being rubbed off with mild abrasion.

Example 23

Polyacrylic Acid With Glycerin

Polyacrylic acid ("PAA") and glycerine were added to deionized water to make a 1% PAA and 75% glycerine solution.

Example 24

Grey Hair Colored With Glycerin Solutions

The procedure set forth in Example 22 was performed using the PAA/glycerine solution prepared as described in Example 23. The hair was colored black and was resistant to washing with shampoo and being rubbed off with mild abrasion.

Example 25

Polyacrylic Acid With Raised pH

A 1 molar solution of sodium hydroxide was added to a solution of 1% PAA to raise the pH from 3 to 5.

Example 26

Grey Hair Colored Using PAA With pH of 5

The procedure set forth in Example 22 was performed using the acidified PAA solution prepared as described in Example 25. The hair was colored black and was resistant to washing with shampoo and being rubbed off with mild abrasion.

Example 27

Grey Hair Colored Without a PAA Step

The carbon black color solution from Example 21 was brushed onto a hair swatch of 50% grey hair and 50% black hair until all the individual hairs appeared black. Then the hair was thoroughly rinsed with water using mild abrasion. Then the color solution was reapplied in the same manner and thoroughly rinsed again. Then approximately 1 mL of the chitosan/silicone emulsion from Example 10 was added to the hair using a pipette, and then it was dried using a hair drier. The hair was colored black and the color was resistant to being removed by washing with shampoo and was resistant to being rubbed off with mild abrasion.

Example 28

Carbon Black Slurry With BPEI, Slurry No. 2

2.75 gm of carbon black were added to 75 g of glycerin. 7 mL deionized water were added to 55 mg of BPEI, and this solution was then added to the carbon black and glycerin. To this slurry, 30 g of ceramic mixing beads were added. The slurry was then bead-milled for 5 minutes on a FlakTek Model DAC 150 FVZ-K. A viscous dispersion of carbon black was obtained.

Example 29

Carbon Black With BPEI Slurry No. 2 on Grey Hair

The procedure set forth in Example 14 was performed using the carbon black slurry prepared as described in Example 28. The hair was colored black and was resistant to washing with shampoo and to being rubbed off with mild abrasion.

Example 30

Chitosan Cationic Sealant (cg800 Chitosan)

A 2% solution of chitosan (cg800) that had been solvated with hydrochloric acid was added to SF8411 silicone and deionized water, and then was homogenized to make an emulsion containing 0.5% chitosan and 0.5% silicone.

Example 31

Carbon Black on Grey Hair using cg800 Chitosan Sealant

The carbon black color solution from Example 28 was brushed onto a hair swatch of 50% grey hair and 50% black hair until all the individual hairs appeared black. Then the hair was thoroughly rinsed with water. Then approximately 1 mL of the 1% PAA solution from Example 9 was added to the hair using a pipette. This was worked in using fingers, and then it was rinsed out. The coloring step and the PAA sealing step as described above were each repeated, with a water rinse in between the two steps. Then approximately 1 mL of the chitosan/silicone emulsion from Example 30 was added to the hair using a pipette, and then it was dried using a hair drier. The hair was colored black and the color was resistant to washing with shampoo and to being rubbed off with mild abrasion.

Example 32

Chitosan Sealant With No Silicone

The carbon black color solution from Example 28 was brushed onto a hair swatch of 50% grey hair and 50% black hair until all the individual hairs appeared black. The hair was then thoroughly rinsed with water. Then approximately 1 mL of the 1% PAA solution from Example 9 was added to the hair using a pipette. This was worked in using fingers, and then it was rinsed out. Then the coloring step and the PAA sealing step were each repeated once again with a water rinse in between the two. Then approximately 1 mL of a 0.5% cg800 chitosan that had been solvated with hydrochloric acid was added to the hair using a pipette, and then it was dried using a hair drier. The hair was colored black, and the color was resistant to washing with shampoo and to being rubbed off with mild abrasion.

Example 33

Carbon Black Slurry With Fumed Silica 3.75 gm of carbon black and 110 mg of BPEI were added to 67.5 mL of water. To this slurry, 30 g of ceramic mixing beads were added. The slurry was then bead-milled for 5 minutes on a FlakTek Model DAC 150 FVZ-K. Then 2.75 g of fumed silica were added and then stirred in the FlackTek for 5 more minutes. A dispersion of viscous carbon black was obtained.

Example 34

Carbon Black Silica Slurry on Hair

The procedure set forth in Example 31 was performed using the carbon black slurry prepared as described in Example 33. The hair was colored black, and was resistant to washing with shampoo and resistant to being rubbed off with mild abrasion.

Example 35

Treatment Protocol With Crosslinking Step

A hair sample is soaked in 0.1M citric acid for 5 minutes. A color dispersion is prepared using 3.75 gm of the carbon black mixed with a BPEI solution of 110 mg BPEI and 71.14 gm deionized water. The color dispersion is brushed onto the hair sample and is worked through the sample manually. Shortly thereafter, the sample is rinsed with warm tap water until it runs clear, typically about 4-5 seconds. The BPEI solution used previously is mixed with a 4% solution of PEG-DGE in equal volumes in a small vial. This mixture is applied to the hair sample, and is dried partially with a heat gun or commercial hair dryer for about 3-5 min. while combing the hair and working the color in with the hands. This drying step stops when the hair becomes too sticky or stiff to comb. A mixture is then prepared using 2% cg800 and 4% PEG-DGE in equal volumes in a small vial. This second mixture is applied to the hair sample and dried similarly, with a heat gun or commercial hair dryer for about 3-5 min. while combing the hair and working the color in with the hands. This drying step stops when the hair becomes too sticky or stiff to comb. The hair is allowed to hang-dry until stiff. The hair is then washed once with shampoo to soften it and to remove the stiff plastic feeling. Use of a commercial hair conditioner can also be added to improve the feel.

Example 36

Carbon Black Slurry With Crosslinking Polyethylene Glycol Diglycidyl Ether (PEG-DGE)

3.75 g of carbon black, 110 mg of BPEI, and 1.5 g PEG-DGE were added to 69.64 g of water. To this slurry, 30 g of ceramic mixing beads were added. The slurry was then bead-milled for 5 minutes on a FlakTek Model DAC 150 FVZ-K. A dispersion of carbon black with epoxy crosslinker was obtained.

Example 37

Carbon Black Slurry Applied to Blonde Hair With Crosslinking PEG-DGE

A blonde hair sample was soaked in 0.1M citric acid for 5 minutes, removed and wrung dry. The carbon black slurry prepared in Example 36 was applied to the hair with a brush and rubbed in with hands. The swatch was rinsed thoroughly in the sink with warm tap water. 4 ml of a mixture of 25% BPEI and 2% PEG-DGE (w/v) in water was applied to the hair and rubbed in by hand. The hair swatch was then heated with a hair dryer for several minutes, with combing. 4 ml of a mixture of 1% cg800 and 2% PEG-DGE (w/v) in water was applied to the hair and rubbed in by hand. The hair swatch was then dried with a hair dryer for several minutes, with combing. After complete drying, the hair sample was washed with shampoo and allowed to air-dry. The colored sample was dark black in color and felt soft and natural. The color is stable to multiple vigorous washes with shampoo and conditioner.

Example 38

Preparation of Crosslinker and Polyamine Emulsion 300 mg PEG-DGE, 1.0 gm BPEI, and 3.0 gm PDMS-epoxy were emulsified in 20 ml decamethylcyclopentasiloxane (DMCPS), by vortexing and shaking vigorously.

Example 39

Emulsion of Crosslinker and Polyamine and Color Dispersion Applied to Blonde Hair A dispersion of carbon black with epoxy crosslinker was prepared according to the method of Example 36. It was applied to a blonde hair sample with brush and worked in with hands. The hair swatch was then rinsed thoroughly in the sink with warm tap water. 10 ml of the emulsion prepared in Example 38 was then applied to the hair sample and completely dried with hair dryer. After complete drying, the hair sample was washed with shampoo and allowed to air-dry. The colored sample was dark black in color and felt soft. The color was stable to multiple vigorous washes with shampoo and conditioner.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless the context otherwise clearly dictates, the words "a" and "an" as used herein are interchangeable with the phrase "one or more".

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the present invention.

What is claimed is:

1. A method for coupling hair with pigment, comprising:
   treating hair with a treatment formulation, the treatment formulation comprising a pigment-functionalized cationic polymer; and
   coupling the treatment formulation to the hair.

2. The method of claim 1, wherein the step of treating hair comprises serially treating hair with a plurality of treatment formulations, each treatment formulation comprising at least one pigment-functionalized cationic polymer, each pigment functionalized cationic polymer being capable of being coupled to the hair.

3. The method of claim 1, further comprising:
   applying at least one sealing composition to the hair after at least one treatment formulation treats the hair to enhance coupling of the at least one treatment formulation to the hair, the sealing composition comprising an anionic component.

4. The method of claim 3, wherein the step of applying at least one sealing composition comprises applying a plurality of sealing compositions to the hair, each sealing composition being applied after at least one step of treating hair with the treatment formulation.

5. The method of claim 3 wherein the anionic component comprises a polyanion.

6. The method of claim 5, wherein the polyanion comprises at least one of maleic anhydride group and carboxylic acid group.

7. The method of claim 5, wherein the polyanion comprises at least one of poly(isobutylene-alt-maleic acid), poly(isobutylene-alt-maleic anhydride), pectin, xanthan gum, carboxy methyl cellulose, polyacrylic acid, and styrene maleic anhydride.

8. The method of claim 3, wherein the step of applying at least one sealing composition comprises increasing abrasion-resistance of the at least one of the treatment formulations.

9. The method of claim 3, wherein the step of applying at least one sealing composition comprises increasing hydrophobicity of the hair relative to not applying the at least one sealing composition.

10. The method of claim 3, further comprising:
    performing at least one of rinsing hair and drying hair after the step of treating the hair but before the step of applying at least one sealing composition.

11. The method of claim 1, further comprising:
    applying a final coating formulation to the hair after the step of treating hair.

12. The method of claim 11, wherein the final coating formulation comprises an emulsified hydrophobic component.

13. The method of claim 11, wherein the final coating formulation comprises at least one of a silicone-containing component, a hydrophobic macromer, a polycation, and a plasticizer.

14. The method of claim 11, wherein the final coating formulation comprises an amine group and a silicone group.

15. The method of claim 11, wherein the final coating formulation comprises a crosslinker.

16. The method of claim 1, wherein the pigment-functionalized cationic polymer is crosslinked.

17. The method of claim 1, wherein the pigment-functionalized cationic polymer comprises an amine-containing polymer.

18. The method of claim 1, wherein the pigment-functionalized cationic polymer comprises at least one of chitosan, polyalkyleneimene, poly(vinyl amine), poly(allyl amine), poly(lysine), cationic cellulose derivatives, and cationic starch derivatives.

19. The method of claim 1, wherein the treatment formulation comprises at least one of an aqueous solvent, an alcoholic solvent, a siloxane-containing solvent.

20. The method of claim 1, wherein the treatment formulation comprises at least one of a surfactant, a foam, a UV blocker, a fragrance, a viscosity modifier, and a crosslinker.

21. The method of claim 1, wherein the treatment formulation comprises a crosslinker capable of crosslinking the pigment-functionalized cationic polymer.

22. The method of claim 1, further comprising:
    pretreating the hair with at least one of an acidic composition and a basic composition before the step of treating the hair with the treatment formulation.

23. The method of claim 22, wherein the at least one of an acidic composition and a basic composition exhibits a pH above about 7.5 or below about 5.5.

24. A kit for coupling pigment to hair comprising:
    a treatment formulation comprising pigment particles coupled to a cationic polymer, the treatment formulation effective for imparting color to hair; and
    a sealing composition comprising an anionic component, the sealing composition effective for enhancing coupling of the pigment-functionalized cationic polymer to hair,
    each formulation being separately packaged.

25. The kit of claim 24, wherein the treatment formulation comprises a plurality of treatment formulations, each treatment formulation comprising pigment particles coupled to at least one type of cationic polymer, each treatment formulation being separately packaged.

26. The kit of claim 24, wherein the sealing composition comprises a plurality of sealing compositions, each sealing composition comprising at least one anionic component, each sealing composition being separately packaged.

27. The kit of claim 24, wherein the anionic component comprises a polyanion.

28. The kit of claim 27, wherein the polyanion comprises at least one of poly(isobutylene-alt-maleic acid), poly(isobutylene-alt-maleic anhydride), pectin, xanthan gum, carboxy methyl cellulose, polyacrylic acid, and styrene maleic anhydride.

29. The kit of claim 24, further comprising:
    a final coating formulation comprising at least one of wherein the final coating formulation comprises at least one of a silicone-containing component, a hydrophobic macromer, a polycation, and a plasticizer, the final coating formulation being packaged separately from the treatment formulation and the sealing composition.

30. The kit of claim 24, wherein the final coating formulation further comprises a crosslinker.

31. The kit of claim 24, wherein cationic polymer comprises at least one of chitosan, polyalkyleneimene, poly(vinyl amine), poly(allyl amine), poly(lysine), cationic cellulose derivatives, and cationic starch derivatives.

32. The kit of claim 24, wherein the treatment formulation comprises at least one of an aqueous solvent, an alcoholic solvent, and a siloxane-containing solvent.

33. The kit of claim 24, wherein the treatment formulation comprises at least one of a surfactant, a foam, a UV blocker, a fragrance, a viscosity modifier, and a crosslinker.

34. The kit of claim 24, wherein the treatment formulation comprises a crosslinker.

35. The kit of claim 24, further comprising:
a pretreatment composition comprising at least one of an acidic composition and a basic composition, the pretreatment composition packaged separately from the treatment formulation and the seal composition.

36. The kit of claim 35, wherein the at least one of an acidic composition and a basic composition exhibits a pH above about 7.5 or below about 5.5.

* * * * *